(12) United States Patent
Weise et al.

(10) Patent No.: US 6,624,241 B2
(45) Date of Patent: *Sep. 23, 2003

(54) WATERBORNE COATING COMPOSITIONS CONTAINING MATERIALS DISPERSED WITH WATER-SOLUBLE CARBAMATE MATERIALS

(75) Inventors: Robert D. Weise, Harper Woods, MI (US); Walter H. Ohrbom, Hartland Township, MI (US); Patricia A. Herrel, Hartland Township, MI (US); David J. Law, Livonia, MI (US)

(73) Assignee: BASF Corporation, Southfield, MI (US)

( * ) Notice: Subject to any disclaimer, the term of this patent is extended or adjusted under 35 U.S.C. 154(b) by 3 days.

This patent is subject to a terminal disclaimer.

(21) Appl. No.: 10/061,013

(22) Filed: Jan. 30, 2002

(65) Prior Publication Data

US 2002/0086966 A1 Jul. 4, 2002

Related U.S. Application Data

(63) Continuation-in-part of application No. 09/970,752, filed on Oct. 4, 2001, now Pat. No. 6,566,476, which is a division of application No. 09/316,591, filed on May 21, 1999, now Pat. No. 6,346,591, which is a continuation-in-part of application No. 10/002,807, filed on Nov. 2, 2001.

(51) Int. Cl.[7] ............................................. C08G 18/06
(52) U.S. Cl. ................. 524/591; 428/423.1; 428/425.8; 428/474.4; 428/500; 524/501; 524/589
(58) Field of Search ........................ 428/423.1, 474.4, 428/500, 425.8; 524/591, 501, 589

(56) References Cited

U.S. PATENT DOCUMENTS

| 2,806,838 A | 9/1957 | Melamed ................... 260/77.5 |
| 3,674,838 A | 7/1972 | Nordstrom .............. 260/482 C |
| 4,126,747 A | 11/1978 | Cowherd, III et al. ...... 520/166 |
| 4,925,885 A | 5/1990 | Rosthauser et al. ......... 524/415 |
| 5,292,833 A | 3/1994 | Grahe et al. ................. 525/531 |
| 5,336,566 A | 8/1994 | Rehfuss ....................... 428/524 |
| 5,356,669 A | 10/1994 | Rehfuss et al. ........... 427/407.1 |
| 5,451,656 A | 9/1995 | Menovcik et al. ........... 528/288 |
| 5,508,379 A | 4/1996 | Menovcik et al. ........... 528/367 |
| 5,512,639 A | 4/1996 | Rehfuss ....................... 428/524 |
| 5,532,061 A | 7/1996 | Menovcik et al. ........ 428/423.1 |
| 5,639,828 A | 6/1997 | Briggs et al. ................ 525/208 |
| 5,693,723 A | 12/1997 | Green ......................... 525/481 |
| 5,693,724 A | 12/1997 | Green ......................... 525/481 |
| 5,792,810 A | 8/1998 | Menovcik et al. ........... 524/590 |
| 6,262,297 B1 | 7/2001 | Clements et al. ........... 560/157 |
| 6,309,707 B1 | 10/2001 | Mayer et al. ................ 427/386 |
| 6,403,709 B2 | 6/2002 | Ramesh et al. ................ 525/95 |
| 2002/0010254 A1 | 1/2002 | Ramesh et al. ............. 524/401 |
| 2002/0132921 A1 | 9/2002 | Ramesh et al. ................ 525/88 |

FOREIGN PATENT DOCUMENTS

| DE | 44 21 823 | 1/1996 |
| EP | 201 715 | 4/1986 |
| GB | 816 985 | 1/1957 |
| WO | WO99/21904 | 5/1999 |
| WO | WO 00/26313 | 5/2000 |
| WO | WO 00/71505 | 5/2000 |
| WO | WO 01/44391 | 6/2001 |

OTHER PUBLICATIONS

Swaminathan Ramesh et al., USSN 09/747,473, filed Dec. 22, 2000, entitled "Water–based Coating composition having carbamate–melamine cross–linking method of preparing the same, and a cured film thereof" pp. 1–39, and the abstract.

BASF Corporation, et al., International Search Report PCT/US02/12787, International Filing Date Apr. 24, 2002.

*Primary Examiner*—Fred Zitomer
(74) *Attorney, Agent, or Firm*—Anna M. Budde

(57) ABSTRACT

The invention provides an aqueous coating composition containing a dispersed, emulsified, or dissolved material (organic compound, resin, or polymer), in which the material is dispersed, emulsified, or dissolved with a water-soluble, carbamate-functional material. The invention further provides a coating prepared from the coating composition and a coated substrate, especially an automotive substrate, having the coating thereon.

29 Claims, No Drawings

WATERBORNE COATING COMPOSITIONS CONTAINING MATERIALS DISPERSED WITH WATER-SOLUBLE CARBAMATE MATERIALS

CROSS-REFERENCE TO RELATED APPLICATIONS

This application is a continuation-in-part of U.S. patent application Ser. No. 09/970,752, filed Oct. 4, 2001, now U.S. Pat. No. 6,566,476 which is a divisional of U.S. patent application Ser. No. 09/316,591, filed May 21, 1999, now U.S. Pat. No. 6,346,591 entitled "Monomer and Polymerization Process," and this application is also a continuation-in-part of U.S. patent application Ser. No. 10/002,807, filed Nov. 2, 2001, entitled "Water- and Organic-Soluble Carbamate Material," the disclosures of each of which are incorporated herein by reference.

FIELD OF THE INVENTION

This invention concerns aqueous coating compositions containing polymers dispersed by water-soluble materials, especially curable coating compositions.

BACKGROUND OF THE INVENTION

Carbamate-functional materials have found particular utility in coating compositions as crosslinkable resins. Curable coating compositions utilizing carbamate-functional resins are described, for example, in U.S. Pat. Nos. 5,693,724, 5,693,723, 5,639,828, 5,512,639, 5,508,379, 5,451,656, 5,356,669, 5,336,566, and 5,532,061, each of which is incorporated herein by reference. These coating compositions can provide significant advantages over other coating compositions, such as hydroxy-functional acrylic/melamine coating compositions. For example, the coatings produced using carbamate-functional resins typically have excellent resistance to environmental etch (also called acid etch). Environmental etch results in spots or marks on or in the coating that often cannot be rubbed out.

One drawback of coatings with carbamate-functional resins is that they tend to require more organic solvent to achieve acceptable viscosity and for application. Carbamate-functional materials prepared from an isocyanurate of a diisocyanate, for example, are generally advantageous as an additive resin or principal resin in a coating composition, but these materials increase the viscosity of the coating composition so that more solvent is required. Coatings with higher amounts of organic solvent are undesirable because they produce more regulated emissions during application.

Aqueous coating compositions have gained prominence due to the regulations on organic emissions. Such coatings have tended to be water-sensitive, however, because of the presence of the hydrophilic groups used to disperse the binder resins or the surfactants, such as polyether-based surfactants, that remain in the coating film as low molecular weight, hydrophilic materials.

It would be advantageous to use a water-soluble, carbamate-functional material to emulsify, disperse, or aid in dissolving binder resins or polymers in an aqueous coating composition because the carbamate-functional material, in particular the carbamate group that accounts for its water solubility, could become part of the cured coating and would then not cause water-sensitivity in the cured coating.

SUMMARY OF THE INVENTION

The invention provides an aqueous coating composition containing a dispersed, emulsified, or dissolved resin or polymer, in which the dispersant for, emulsifier for, or aid for dissolving the resin or polymer is a water-soluble, carbamate-functional material. The invention further provides a coating prepared from the coating composition and a coated substrate, especially an automotive substrate, having the coating thereon.

The water-soluble, carbamate-functional materials of the invention have a sufficient number of β-hydroxy carbamate groups to be soluble in water. The water-soluble, carbamate-functional materials may be dissolved in water at ambient temperature or in warm water, with the water being heated up to perhaps about 50° C. The β-hydroxy carbamate groups have the isomeric structures

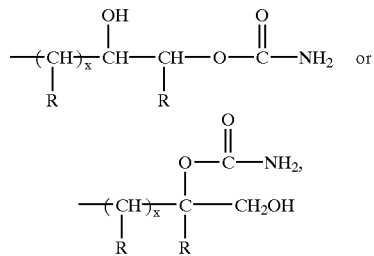

wherein each R is independently hydrogen, methyl, or ethyl and x is an integer of 1 to 3. Preferably, R is in each case a hydrogen and x is 1.

In one embodiment, the water-soluble, carbamate-functional materials may be represented by a structure

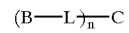

in which B represents β-hydroxy carbamate groups having the above structures; L represents a linking group formed with a hydrogen acceptor group; C represents an n-functional central moiety; and n is a positive integer. The carbamate groups are primary carbamate groups, i.e. there are two nitrogen hydrogens.

The central moiety C has up to about 6 carbon atoms per β-hydroxy carbamate group, preferably up to about 4.5 carbons per β-hydroxy carbamate group, more preferably up to about 4.0 carbons per β-hydroxy carbamate group, and still more preferably up to about 3.0 carbons per β-hydroxy carbamate group. In terms of the structure, the number of carbons of the C group may be represented by up to 6·n, preferably up to 4.5·n, more preferably up to 4.0·n, and still more preferably up to 3.0·n. For some applications, such as automotive topcoats, particularly automotive clearcoats, the C group is preferably aliphatic. In some preferred embodiments the C group includes an aliphatic ring.

The aqueous coating composition also includes at least a second component, which may be an organic compound, resin, and/or polymer, that is brought into the aqueous coating composition using the β-hydroxy carbamate material. The second component may be dispersed, emulsified, or form a homogenous aqueous phase. For purposes of this invention, no distinction will be made between "dispersions" and "emulsions," and those terms may be used herein as synonyms. The second component may have some water solubility, but is not completely water soluble and is less water soluble than the β-hydroxy carbamate material. Thus, in one embodiment, the second component may partially dissolve in water without using the β-hydroxy carbamate material, but the β-hydroxy carbamate material can be used to bring the second component into the aqueous medium to form a stable, clear medium that does not phase separate over time. The second component may be, for example, any organic compound, resin, or polymer suitable for coating compositions, including especially film-forming materials such as crosslinking agents which may cure the water-soluble, carbamate-functional material under appropriate curing conditions, curable polymers, curable oligomers, and curable compounds, especially curable materials having active hydrogen functionality.

Preferably, the coating composition is curable, and preferably both the second component and the β-hydroxy carbamate material crosslink during curing of the coating composition.

DETAILED DESCRIPTION OF THE PREFERRED EMBODIMENTS

The following description of the preferred embodiment(s) is merely exemplary in nature and is in no way intended to limit the invention, its application, or uses.

In one embodiment, the water-soluble, carbamate-functional materials used to disperse the component may be represented by a structure

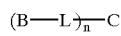

in which B represents β-hydroxy carbamate groups having the structures

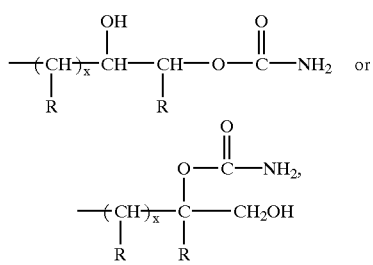

wherein each R is independently hydrogen, methyl, or ethyl, preferably hydrogen and x is an integer of 1 to 3, preferably 1; L represents a linking group formed by a hydrogen acceptor group; C represents an n-functional central moiety; and n is a positive integer, preferably from 1 to about 8, more preferably at least two, even more preferably from 2 to about 4.

Suitable examples of the linking group L include, without limitation,

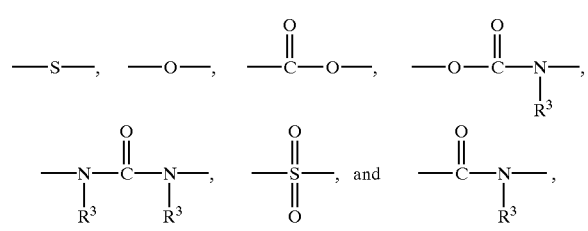

with one free bond of each group connected to B and the other free bond connected to C.

In one embodiment of the invention, the water-soluble, carbamate-functional material may be a homopolymer having a monomer unit represented by the structure

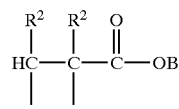

in which each $R^2$ is independently H or methyl and B is as defined above, or a monomer unit

in which B is as defined above.

The water-soluble, carbamate-functional material may also be a copolymer having the monomer unit just described and having a fraction of different monomer units, particularly hydrophilic monomer units, in an amount so that the copolymer is water-soluble.

The water-soluble, β-hydroxy carbamate polymer may be the polymerization product of a monomer prepared by reacting a glycidyl-group containing polymerizable monomer first with carbon dioxide to convert the oxirane group to a cyclic carbonate group, and then with ammonia or a primary amine to convert the cyclic carbonate group to a β-hydroxy carbamate group. Examples of suitable oxirane group-containing polymerizable monomers include, without limitation, glycidyl acrylate, glycidyl methacrylate, glycidyl crotonate, and allyl glycidyl ether. Oxirane groups can be converted to carbamate groups by first converting to a cyclic carbonate group by reaction with $CO_2$. This can be done at any pressure from atmospheric up to supercritical $CO_2$ pressures, but is preferably under elevated pressure (e.g., 60–150 psi). The temperature for this reaction is preferably 60–150° C. Useful catalysts include any that activate an oxirane ring, such as tertiary amine or quaternary salts (e.g., tetramethyl ammonium bromide), combinations of complex organotin halides and alkyl phosphonium halides (e.g., $(CH_3)_3SnI$, $Bu_4SnI$, $Bu_4PI$, and $(CH_3)_4PI$), potassium salts (e.g., $K_2CO_3$, KI) preferably in combination with crown ethers, tin octoate, calcium octoate, and the like.

The cyclic carbonate group is reacted with ammonia. The ammonia may be aqueous ammonia (i.e., $NH_4OH$). The reaction ring-opens the cyclic carbonate to form a β-hydroxy carbamate monomer.

The polymerization of the monomer preferably is carried out in water or in an a mixture that includes water. The β-hydroxy carbamate monomer may be polymerized in the presence of free-radical initiators or with a redox initiator system. Useful initiators and redox initiator systems are well-known. The polymerization may be carried out without solvent or in an organic or aqueous medium. In a preferred embodiment, the β-hydroxy carbamate monomer is polymerized in an aqueous medium, preferably without any organic solvent or with a minor amount (up to about 10% by weight of the aqueous medium) of a polar solvent such as methanol, tetrahydrofuran, propylene glycol monomethyl ether, or other water-soluble or water-miscible solvents. The β-hydroxy carbamate monomer may be dissolved in water along with the initiating system and polymerized at a suitable temperature for the initiating system.

In an alternative embodiment, a homopolymer or copolymer including β-hydroxy carbamate units may be prepared by including the corresponding cyclic carbonate monomer and forming the carbamate group from the carbonate group at some time during the polymerization of the corresponding cyclic carbonate monomer. For example, ammonia can be charged to the polymerization reactor and react with the cyclic carbonate group during the polymerization. The reactor can be pressurized for ammonia. The ammonia could also be added during the polymerization reaction.

Examples of homopolymers and copolymers of the β-hydroxy carbamate monomer useful for coating compositions are those that have weight average molecular weights of from about 2500 to over a million.

In another embodiment, the water-soluble, carbamate-functional compound of the invention may have a structure

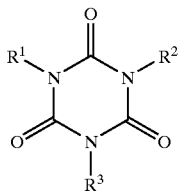

in which each of $R^1$, $R^2$, and $R^3$ is independently

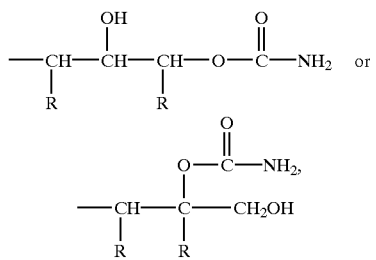

wherein R is hydrogen, methyl, or ethyl.

This water-soluble, β-hydroxy carbamate compound may be prepared by reacting triglycidyl isocyanurate first with carbon dioxide to convert the oxirane groups to cyclic carbonate groups, and then with ammonia to convert the cyclic carbonate group to a β-hydroxy carbamate group. The reactions proceed in the same way as for the monomer synthesis already described. Triglycidyl isocyanurate is commercially available or may be prepared by reaction of isocyanuric acid with an epihalohydrin, in particular epichlorohydrin.

In yet another embodiment, the water-soluble carbamate functional compound of the invention may have a C structure selected from alkylene groups having up to about six carbon atoms per β-hydroxy carbamate group, especially butylene, pentylene, hexylene, and cyclohexylene; and

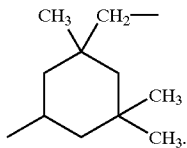

Further examples of water-soluble, β-hydroxy carbamate-functional materials of the invention may be prepared from glycidol carbonate, which has the structure

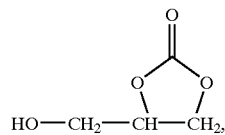

by reacting the hydroxyl group with a compound having a functional group reactive with hydroxyl and then by reacting the product with ammonia to convert the cyclic carbonate group to a β-hydroxy carbamate group. Glycidol carbonate is commercially available or may be prepared by reaction of glycidol with carbon dioxide, using such conditions as already described. Glycidol in turn may be prepared by reaction of allyl alcohol with peroxide. Alternatively, the alcohol group of one of the precursors to glycidol carbonate, either allyl alcohol or glycidol, may be reacted with the compound having a functional group reactive with hydroxyl before synthesis of the carbonate group and then carbamate group. This may be advantageous when the carbonate group may react with the compound having the functional group reactive with hydroxyl, for example if an esterification reaction is contemplated.

Examples of groups reactive with hydroxyl groups include, without limitation, acid groups, anhydride groups, isocyanate groups, lactones, oxirane (epoxide) groups, halides, and combinations of these. The reactions may be carried out under conditions typical for reactions of such groups with hydroxyl-functional compounds.

The allyl alcohol, glycidol, or glycidol carbonate may, for example, be reacted with a carboxylic acid-functional or anhydride-functional compound having up to about 6, preferably up to about 4.5, carbon atoms per carboxylic acid group. Examples of suitable carboxylic acid and anhydride compounds include, without limitation, monocarboxylic acids such as butanoic acid; hydroxycarboxylic acids such as dimethylolpropionic acid; polycarboxylic acids such as phthalic acid, isophthalic acid, terephthalic acid, alkyl-substituted phthalic, isophthalic, and terephthalic acids; maleic acid, fumaric acid, itaconic acid, malonic acid, tetrahydrophthalic acid, hexahydrophthalic acid, and alkyl-substituted partially or fully hydrogenated phthalic, isophthalic, and terephthalic acids.

The esterification reaction can be conducted under typical esterification conditions, for example at temperatures from room temperature up to about 150° C., and with catalysts such as, for example, calcium octoate, metal hydroxides like potassium hydroxide, Group I or Group II metals such as sodium or lithium, metal carbonates such as potassium carbonate or magnesium carbonate (which may be enhanced by use in combination with crown ethers), organometallic oxides and esters such as dibutyl tin oxide, stannous octoate, and calcium octoate, metal alkoxides such as sodium methoxide and aluminum tripropoxide, protic acids like sulfuric acid, or $Ph_4Sbl$. The reaction may also be conducted at room temperature with a polymer-supported catalyst such as Amerlyst-15® (available from Rohm & Haas) as described by R. Anand in *Synthetic Communications*, 24(19), 2743–47 (1994), the disclosure of which is incorporated herein by reference.

The allyl alcohol, glycidol, or glycidol carbonate may also be reacted with an isocyanate-functional compound. Examples of suitable isocyanate-functional compounds include, without limitation, monofunctional isocyanate compounds and polyisocyanates having up to about 6 carbons atoms, preferably up to about 4.5 carbon atoms, per isocyanate group. Suitable examples of these include, without limitation, ethylene diisocyanate, 1,2-diisocyanatopropane, 1,3-diisocyanatopropane, 1,6-diisocyanatohexane (hexamethylene diisocyanate or HMDI), 1,4-butylene diisocyanate, cyclohexane-1,3- and -1,4-diisocyanate, 1,4-methylene bis-(cyclohexyl isocyanate), isophorone diisocyanate (IPDI), the various isomers of tolylene diisocyanate, 4,4'-dibenzyl diisocyanate, and 1,2,4-benzene triisocyanate, and so on.

The reaction of the allyl alcohol, glycidol, or glycidol carbonate with the isocyanate-functional compound can be conducted under typical conditions for forming urethane linkages, for example at temperatures from room temperature up to about 150° C., and with catalysts such as, for example, tin catalysts including dibutyl tin dilaurate, dibutyl tin oxide, and the like.

The coating composition also includes at least one second component, preferably a film-forming, curable compound, resin, or polymer, that is emulsified, dispersed, or dissolved using the β-hydroxy carbamate material. The second component may be any compound, resin, or polymer suitable for coating compositions, including crosslinking agents that may cure the water-soluble, carbamate-functional material under appropriate curing conditions, curable polymers, curable oligomers, and curable compounds, especially curable materials having active hydrogen functionality.

The second component may have some water solubility, but is not completely water soluble and is less water soluble than the β-hydroxy carbamate material. Thus, in one embodiment, the second material may partially dissolve in water without using the β-hydroxy carbamate material, but the β-hydroxy carbamate material can be used to bring the second material into the aqueous medium to form a stable, clear medium that does not phase separate over time. The second material need not have any water solubility, and water solubility is even undesirable if the groups providing the water solubility as not substantially reacted into the cured coating (that is, if such groups remain to cause the cured coating to be water sensitive) or if stability of the coating composition is compromised.

Preferred polymers that may be dispersed by the water-soluble, carbamate-functional material include, without limitation, acrylic polymers, modified acrylic polymers, polyesters, polyepoxides, polycarbonates, polyurethanes, polyamides, polyimides, and polysiloxanes, all of which are well-known in the art. Preferably, the second polymer is an acrylic, modified acrylic, or polyester. More preferably, the second polymer is an acrylic resin. The acrylic resin preferably has a number average molecular weight of 500 to 1,000,000, and more preferably of 1500 to 50,000. Number average molecular weight may be determined by the GPC method using a polystyrene standard. Such polymers can be prepared from monomers such as methyl acrylate, acrylic acid, methacrylic acid, methyl methacrylate, butyl methacrylate, cyclohexyl methacrylate, and the like. A curable functional group can be incorporated into the ester portion of the acrylic monomer. For example, hydroxy-functional acrylic monomers that can be used to form such polymers include hydroxyethyl acrylate, hydroxybutyl acrylate, hydroxybutyl methacrylate, hydroxypropyl acrylate, and the like; amino-functional acrylic monomers include t-butylaminoethyl methacrylate or t-butylaminoethyl acrylate; acid-functional monomers include acrylic acid, methacrylic acid, and itaconic acid; epoxide-functional monomers include glycidyl acrylate and glycidyl methacrylate; and so on. Carbamate-functional acrylic polymers may also be used, and well as polymers having a combination different kinds of functional groups.

Modified acrylics can also be emulsified or dispersed. Modified acrylics may be polyester-modified acrylics or polyurethane-modified acrylics, both of which are well-known in the art. Polyester-modified acrylics modified with ε-caprolactone are described in Etzell et al., U.S. Pat. No. 4,546,046, which is incorporated herein by reference. Polyurethane-modified acrylics are described, for example, in U.S. Pat. No. 4,584,354, which is incorporated herein by reference.

Polyesters having epoxide groups or active hydrogen groups such as hydroxyl groups, acid groups, or carbamate groups can also be used as the polymer dispersed in the composition to the invention. Such polyesters are well-known in the art, and may be prepared by the polyesterification of organic polycarboxylic acids (e.g., phthalic acid, hexahydrophthalic acid, adipic acid, maleic acid) or their anhydrides with organic polyols containing primary or secondary hydroxyl groups (e.g., ethylene glycol, butylene glycol, neopentyl glycol). Carbamate-functional polyesters are disclosed in U.S. Pat. Nos. 5,508,379, 5,451,656, and 5,532,061, the disclosures of each of which is incorporated herein by reference. Polyesters having epoxide groups may be formed from unsaturated polyesters by reaction with peroxide, e.g., hydrogen peroxide, or from hydroxyl- or acid-functional polyesters by reaction with an epihalohydrin compound, followed by the carbamate synthesis already described.

Polyurethanes having active hydrogen functional groups are also suitable as a polymers emulsified or dispersed in the compositions of the invention. Such polyurethanes are well-known in the art. They may be prepared by a chain extension reaction of a polyisocyanate (e.g., hexamethylene diisocyanate, isophorone diisocyanate, MDI, etc.) and a polyol (e.g., 1,6-hexanediol, 1,4-butanediol, neopentyl glycol, trimethylolpropane, polyester polyol, polyether polyol). They can be provided with active hydrogen functional groups by capping the polyurethane chain with an excess of diol, polyamine, amino alcohol, or the like. Polyurethanes having epoxide groups may be formed from unsaturated polyurethanes or from hydroxyl- or acid-functional polyurethanes according to the methods described above for synthesis of component (a). Acid-functional polyurethanes may be synthesized by including a monomer having acid functionality, such as, without limitation, dimethylolpropionic acid. The hydroxyl groups react to form the urethane linkages while the acid group remains unreacted in the polyurethane polymerization.

In one embodiment, the second component may include a carbamate- or urea-functional material, resin, or polymer, including a β-hydroxy carbamate-functional material. A carbamate group may be represented by the structure

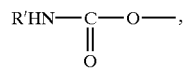

in which R' is H or alkyl. Preferably, R' is H or alkyl of from 1 to about 4 carbon atoms, and more preferably R' is H (a primary carbamate). A urea group may be represented by the structure

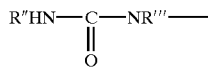

in which R" and R''' are each independently H or alkyl or R" and R''' together form a heterocyclic ring structure. Preferably, R" and R''' are each independently or together form an ethylene bridge, and more preferably R' and R''' are each H (a primary urea). When the second component has β-hydroxy carbamate functionality, the second component is less water soluble that the water-soluble, β-hydroxy carbamate-functional material of the invention. Thus, the β-hydroxy carbamate material of the second component may have more than about six carbons per β-hydroxy carbamate group, not counting the carbons of the β-hydroxy carbamate groups or of linking groups formed by a hydrogen acceptor group.

A carbamate-functional resin or polymer of the second component can be prepared in a variety of ways. Carbamate-functional polyester have already been mentioned. One way to prepare such acrylic polymers is to prepare an acrylic monomer having a carbamate functionality in the ester portion of the monomer. Such monomers are well-known in the art and are described, for example in U.S. Pat. Nos. 3,479,328, 3,674,838, 4,126,747, 4,279,833, and 4,340,497, 5,356,669, and WO 94/10211 which are incorporated herein by reference. One method of synthesis involves reaction of a hydroxy-functional monomer with cyanic acid (which may be formed by the thermal decomposition of urea) to form the carbamyloxy carboxylate (i.e., carbamate-modified (meth) acrylate). Another method of synthesis reacts an α,β-unsaturated acid ester with a hydroxy carbamate ester to form the carbamyloxy carboxylate. Yet another technique involves formation of a hydroxyalkyl carbamate by reacting a primary or secondary amine or diamine with a cyclic carbonate such as ethylene carbonate. The hydroxyl group on the hydroxyalkyl carbamate is then esterified by reaction with acrylic or methacrylic acid to form the monomer. Other methods of preparing carbamate-modified acrylic monomers are described in the art, and can be utilized as well. The acrylic monomer can then be polymerized along with other ethylenically-unsaturated monomers, if desired, by techniques well-known in the art.

An alternative route for preparing a carbamate-functional polymer is to react an already-formed polymer such as an acrylic polymer with another component to form a carbamate-functional group appended to the polymer backbone, as described in U.S. Pat. No. 4,758,632, the disclosure of which is incorporated herein by reference. One technique for preparing polymers useful as the second component involves thermally decomposing urea (to give off ammonia and HNCO) in the presence of a hydroxy-functional acrylic polymer to form a carbamate-functional acrylic polymer with less than complete water solubility, typically no water solubility. Another technique involves reacting the hydroxyl group of a hydroxyalkyl carbamate with the isocyanate group of an isocyanate-functional monomer or polymer to form a carbamate-functional polymer. Isocyanate-functional polyurethanes are formed by polymerization with excess equivalents of isocyanate. Isocyanate-functional acrylics are known in the art and are described, for example in U.S. Pat. No. 4,301,257, the disclosure of which is incorporated herein by reference. Isocyanate vinyl monomers are well-known in the art and include unsaturated m-tetramethyl xylene isocyanate and isocyanatoethyl methacrylate. Yet another technique is to react the cyclic carbonate group on a cyclic carbonate-functional polymer with ammonia or a primary amine in order to form the carbamate-functional acrylic. Cyclic carbonate-functional acrylic polymers are known in the art and are described, for example, in U.S. Pat. No. 2,979,514, the disclosure of which is incorporated herein by reference. Another technique is to transcarbamylate a hydroxy-functional polymer with an alkyl carbamate. A more difficult, but feasible way of preparing the polymer would be to trans-esterify a polymer with a hydroxyalkyl carbamate.

The second component may include a carbamate-functional compound. Such carbamate-functional compounds include, without limitation, any of those described in U.S. Pat. Nos. 6,160,058, 6,084,038, 6.080.825, 5,994,479, the disclosures of which are incorporated by reference. In particular, the composition may include a carbamate-functional or urea-functional material comprising at least two functional groups, at least one of which is a carbamate or urea group that is the reaction product of (1) an hydroxyl group of a first compound that is the result of a ring-opening reaction between a compound with an epoxy group and a compound with an organic acid group and (2) cyanic acid or a carbamate or urea group-containing compound.

In another embodiment, the second component may include a carbamate-functional or urea-functional material that is the reaction product of (1) a compound comprising a carbamate or urea group and an active hydrogen group that is reactive with (2), and (2) a lactone or a hydroxy carboxylic acid. In a particularly preferred embodiment, the active hydrogen group of compound (1) is an hydroxyl group and the compound (2) is ε-caprolactone. The compound (1) may be, for example and without limitation, hydroxyethyl carbamate, hydroxypropyl carbamate, or hydroxybutyl carbamate.

In another embodiment, the second component may include a carbamate-functional or urea-functional material that is the reaction product of a first material (A) that is prepared by reacting (1) a compound comprising a primary carbamate or primary urea group and an hydroxyl group and (2) a lactone or a hydroxy carboxylic acid, as just described, further reacted with a second material (B) that is reactive with hydroxyl groups on a plurality of molecules of compound (1), but that is not reactive with the carbamate or urea groups on compound (1). For example, the compound (B) may be a polyisocyanate, especially an isocyanate, particularly the isocyanurate of isophorone diisocyanate. Again, the compound (2) is preferably ε-caprolactone.

In yet another embodiment, the second component may include a carbamate-functional or urea-functional material that is the reaction product of a first material (A) that is prepared by reacting (1) a compound comprising a primary carbamate or primary urea group and an hydroxyl group and (2) a lactone or a hydroxy carboxylic acid, as just described, further reacted with a second material or materials (B) that converts an hydroxyl group on the reaction product to a carbamate group, or a component comprising a group that is reactive with a hydroxyl group and a carbamate or urea group or group that can be converted to carbamate or urea. The hydroxyl group can be reacted, for example, without limitation, with monoisocyanates such as methyl isocyanate and butyl isocyanate, which react to form a secondary carbamate group; cyanic acid (which can be formed by the thermal decomposition of urea), which reacts with hydroxyl groups to form a primary carbamate group; or phosgene, followed by reaction with ammonia (primary carbamate group) or a primary amine (secondary carbamate group).

In another embodiment, the second component may include a carbamate-functional or urea-functional material that is the reaction product of (1) a compound comprising a primary carbamate or primary urea group and an hydroxyl group and (2) a compound that is reactive with hydroxyl groups on a plurality of molecules of compound (1), but that is not reactive with the carbamate or urea groups on compound (1). The compound (1) may be, for example and without limitation, hydroxyethyl carbamate, hydroxypropyl carbamate, or hydroxybutyl carbamate. The compound (2) is preferably a diisocyanate, triisocyanate, isocyanurate or biuret thereof, mixture of such compounds. Particularly preferred compounds (2) are the isocyanurate of isophorone diisocyanate and the isocyanurate of hexamethylene diisocyanate.

In another preferred embodiment, the second component includes a carbamate-functional or urea-functional material that is the reaction product of (1) a first material that is the reaction product of a mixture including at least a polyisocyanate and an active hydrogen-containing chain extension agent with (2) a compound comprising a group that is reactive with said first material and a carbamate group or group that can be converted to carbamate. Suitable examples of the material (1) include, without limitation, the reaction product of a mixture including at least one of a diisocyanate, triisocyanate, isocyanurate or biuret thereof, mixture of such compounds, and at least one chain extension agent selected from 1,6-hexanediol, cyclohexanedimethylol, 2-ethyl-1,6-hexanediol, 3-hydroxy-2,2-dimethylpropyl 3-hydroxy-2,2-dimethylpropionate, 1,4-butanediol, and mixtures thereof. Suitable examples of compound (2) include, without limitation, hydroxyethyl carbamate, hydroxybutyl carbamate, hydroxypropyl carbamate, and combinations of these.

In a preferred embodiment, the second component includes a material as described in co-pending U.S. patent application Ser. No. 09/741,511, filed Dec. 19, 2000, incorporated herein by reference. The clearcoat coating composition particularly includes a carbamate-functional material having at least two carbamate groups, preferably two to four carbamate groups, and more preferably two carbamate groups and a hydrocarbon moiety with about 24 to about 72 carbon atoms, preferably about 36 to about 72 carbon atoms, and more preferably about 36 to about 54 carbon atoms, and particularly preferably about 36 carbon atoms. The hydrocarbon moiety may include cycloaliphatic or aromatic structures. Such materials may be prepared, for example, by addition reaction of unsaturated monofunctional fatty acids having 12 to 18 carbon atoms according to known methods, followed by conversion of the acid group to a carbamate group. The unsaturated fatty acids may be dimerized, trimerized, or tetramerized. Higher oligomer products are also possible, but not preferred. The acid groups may be converted to carbamate or urea groups by a number of known means. For example, the acid may be reduced to an alcohol group and then the alcohol group reacted with a hydroxy carbamate or urea compound such as hydroxypropyl carbamate or hydroxyethylene ethyl urea to introduce the carbamate functionality. Another method of synthesis involves reaction of an hydroxyl group with cyanic acid (which may be formed by the thermal decomposition of urea). Hydroxyl groups can also be converted to carbamate groups by reaction with low molecular weight monoisocyanates (e.g., methyl isocyanate, ethyl isocyanate, propyl isocyanate, and butyl isocyanate). An hydroxyl group can also be reacted with phosgene and then ammonia or a primary amine to form a carbamate group.

Preferred examples of such materials include compounds of the following structures:

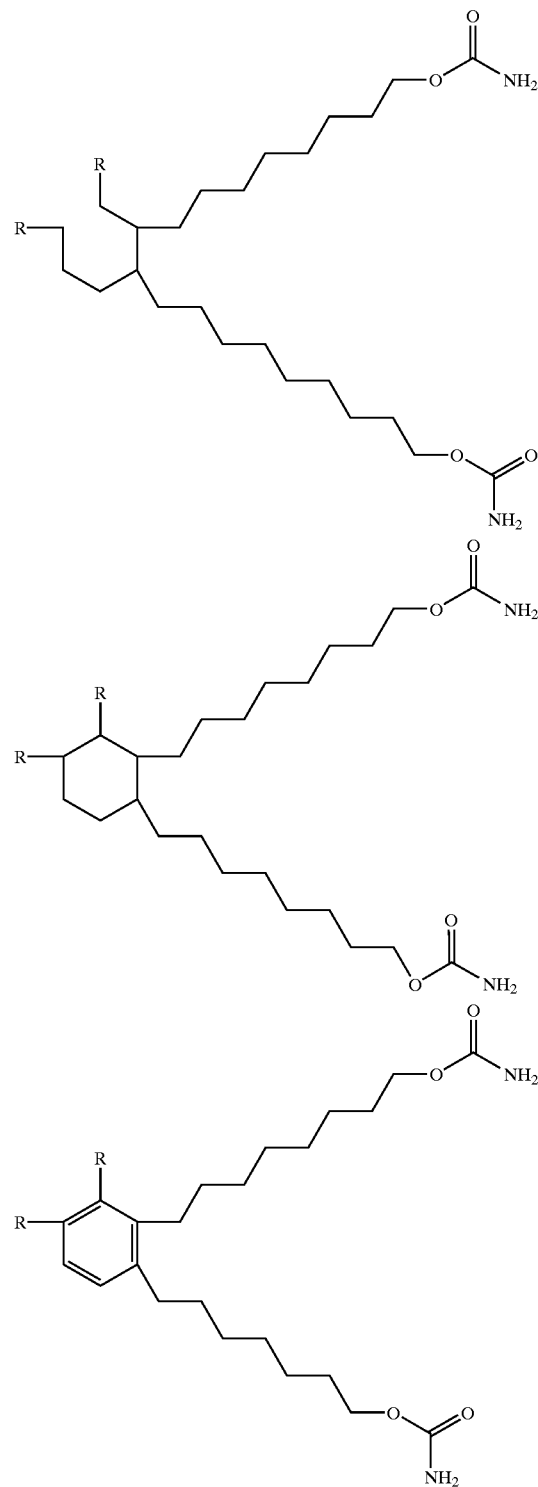

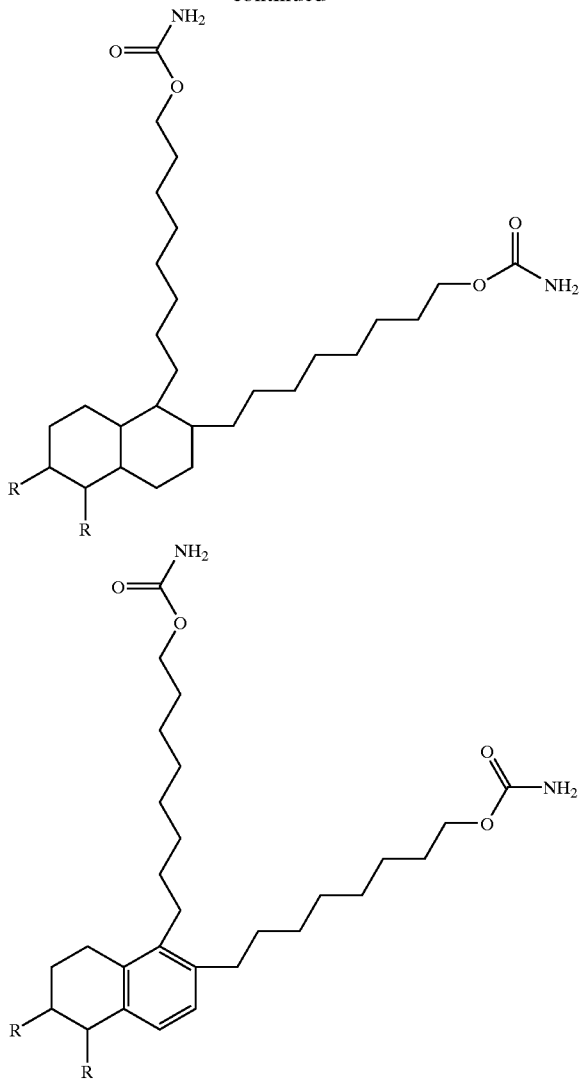

R=C$_5$–C$_8$ wherein each R group is independently an alkyl of 5 to 8 carbon atoms.

The second component may also include mixtures of any of the materials described above as suitable for the second component.

In addition to the water-soluble, β-hydroxy carbamate functional material, the coating composition includes one or more crosslinkers reactive with active hydrogen groups. The crosslinker may be the emulsified or dispersed material or may be included in addition to one or more of the second component materials already described. Particularly useful crosslinkers include, without limitation, materials having active methylol or methylalkoxy groups, such as aminoplast crosslinking agents or phenol/formaldehyde adducts. Examples of preferred curing agent compounds include, without limitation, melamine formaldehyde crosslinkers, including monomeric or polymeric melamine resin and partially or fully alkylated melamine resin, urea resins, and methylol ureas such as urea formaldehyde resin, alkoxy ureas such as butylated urea formaldehyde resin. Another suitable crosslinking agent is tris(alkoxy carbonylamino) triazine (available from Cytec Industries under the trademark TACT). Other useful crosslinkers include, without limitation, polyisocyanates and blocked polyisocyanates, curing agents that have epoxide groups, amine groups, acid groups, siloxane groups, cyclic carbonate groups, and anhydride groups. The curing agent may be combinations of these, particularly combinations that include aminoplast crosslinking agents. At least one crosslinker with functionality reactive with active hydrogens of the β-hydroxy carbamate compound is included. Aminoplast resins such as melamine formaldehyde resins or urea formaldehyde resins are especially preferred. Water-soluble aminoplast resins for aqueous coating compositions are known. These include high imino-content melamine formaldehyde resins and fully methoxylated melamine formaldehyde resins. When the crosslinker is not water-soluble, it may be dispersed using the water-soluble, carbamate-functional material.

In preferred embodiments, the crosslinker is at least about 5%, more preferably at least about 10% by weight of the nonvolatile vehicle. It is also preferred for the crosslinker to be up to about 40%, more preferably up to about 30% by weight of the nonvolatile vehicle. The crosslinker is preferably from about 5% to about 40%, more preferably from about 10% to about 35%, and still more preferably from about 15% to about 35% by weight of the nonvolatile vehicle.

The coating composition used in the practice of the invention may include a catalyst to enhance the cure reaction. For example, when aminoplast compounds, especially monomeric melamines, are used as a curing agent, a strong acid catalyst may be utilized to enhance the cure reaction. Such catalysts are well-known in the art and include, without limitation, p-toluene sulfonic acid, dinonylnaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine. Other catalysts that may be useful in the composition of the invention include Lewis acids, zinc salts, and tin salts.

Although aqueous coating compositions that are free of regulated volatile organic compounds are preferred, a solvent may optionally be utilized in the coating composition used in the practice of the present invention. In general, the solvent can be any organic solvent and/or water. In one preferred embodiment, the solvent is a polar organic solvent. More preferably, the solvent is selected from polar aliphatic solvents or polar aromatic solvents. Still more preferably, the solvent is a ketone, ester, acetate, aprotic amide, aprotic sulfoxide, aprotic amine, or a combination of any of these. Examples of useful solvents include, without limitation, methyl ethyl ketone, methyl isobutyl ketone, m-amyl acetate, ethylene glycol butyl ether-acetate, propylene glycol monomethyl ether acetate, xylene, N-methylpyrrolidone, blends of aromatic hydrocarbons, and mixtures of these. In another preferred embodiment, the solvent is water or a mixture of water with small amounts of co-solvents.

The coating composition according to the invention is preferably utilized in an automotive or industrial high-gloss coating and/or as the clearcoat of an automotive composite color-plus-clear coating. High-gloss coatings as used herein are coatings having a 20° gloss (ASTM D523) or a DOI (ASTM E430) of at least 80.

The coating composition may also be formulated as a pigmented coating, such as for a basecoat coating or a primer coating. In this case, the coating composition further includes a pigment or filler material. The pigment may be any organic or inorganic compounds or colored materials, metallic or other inorganic flake materials such as pearlescent mica flake pigments or metallic flake pigments such as aluminum flake, and other materials of kind that the art normally includes in such coatings. Examples of typical fillers are talc and barytes. Pigments and other insoluble particulate compounds such as fillers are usually used in the composition in an amount of 1% to 100%, based on the total solid weight of binder components (i.e., a pigment-to-binder ratio of 0.1 to 1).

Additional agents, for example surfactants, stabilizers, wetting agents, rheology control agents, dispersing agents, adhesion promoters, UV absorbers, hindered amine light stabilizers, etc. may be incorporated into the coating composition. While such additives are well-known in the prior art, the amount used must be controlled to avoid adversely affecting the coating characteristics.

Coating compositions can be coated on the article by any of a number of techniques well-known in the art. These include, for example, spray coating, dip coating, roll coating, curtain coating, and the like. For automotive body panels, spray coating is preferred.

When the coating composition according to the invention is used as the clearcoat of a composite color-plus-clear coating, the pigmented basecoat composition may any of a number of types well-known in the art, and does not require explanation in detail herein. Polymers known in the art to be useful in basecoat compositions include acrylics, vinyls, polyurethanes, polycarbonates, polyesters, alkyds, and polysiloxanes. Preferred polymers include acrylics and polyurethanes. In one preferred embodiment of the invention, the basecoat composition also utilizes a carbamate-functional acrylic polymer. Basecoat polymers may be thermoplastic, but are preferably crosslinkable and comprise one or more type of crosslinkable functional groups. Such groups include, for example, hydroxy, isocyanate, amine, epoxy, acrylate, vinyl, silane, and acetoacetate groups. These groups may be masked or blocked in such a way so that they are unblocked and available for the crosslinking reaction under the desired curing conditions, generally elevated temperatures. Useful crosslinkable functional groups include hydroxy, epoxy, acid, anhydride, silane, and acetoacetate groups. Preferred crosslinkable functional groups include hydroxy functional groups and amino functional groups.

Basecoat polymers may be self-crosslinkable, or may require a separate crosslinking agent that is reactive with the functional groups of the polymer. When the polymer comprises hydroxy functional groups, for example, the crosslinking agent may be an aminoplast resin, isocyanate and blocked isocyanates (including isocyanurates), and acid or anhydride functional crosslinking agents.

The coating compositions described herein are preferably subjected to conditions so as to cure the coating layer. Although various methods of curing may be used, heat-curing is preferred. Generally, heat curing is effected by exposing the coated article to elevated temperatures provided primarily by radiative heat sources. Curing temperatures will vary depending on the particular blocking groups used in the cross-linking agents, however they generally range between 90° C. and 180° C. The first compounds according to the present invention are preferably reactive even at relatively low cure temperatures. Thus, in a preferred embodiment, the cure temperature is preferably between 115° C. and 150° C., and more preferably at temperatures between 115° C. and 140° C. for a blocked acid catalyzed system. For an unblocked acid catalyzed system, the cure temperature is preferably between 80° C. and 100° C. The curing time will vary depending on the particular components used, and physical parameters such as the thickness of the layers, however, typical curing times range from 15 to 60 minutes, and preferably 15–25 minutes for blocked acid catalyzed systems and 10–20 minutes for unblocked acid catalyzed systems.

The invention is further described in the following example. The examples are merely illustrative and do not in any way limit the scope of the invention as described and claimed. All parts are parts by weight unless otherwise noted.

EXAMPLE OF THE INVENTION

A mixture of 23.8 parts by weight of anhydrous butyl acetate, 24.6 parts by weight of isophorone diisocyanate, and 0.025 parts by weight of dibutyltin dilaurate was heated under an inert atmosphere to 45° C. Then 27.2 parts by weight of 4-hydroxymethyl-1,3-dioxolan-2-one was slowly added. When the reaction was complete, the reaction mixture was cooled to room temperature and 24.3 parts by weight of methanol was added. Keeping the reaction temperature at or below 30° C., ammonia gas was bubbled into the solution. When the reaction was complete, the excess ammonia and solvents were removed by vacuum distillation to provide the synthesis product.

20 parts by weight of the synthesis product and 20 parts by weight of a dicarbamate material prepared according to Example 1, part 1 of U.S. application Ser. No. 09/741,511 were melt-mixed on a hot plate. Then 25 parts by weight of deionized water and 2.9 parts by weight of Nacure 5543 (available from King Industries, Norwalt, Conn.) were added and the mixture was stirred using a laboratory air motor. A viscous, clear liquid was formed. The liquid did not separate over time.

Comparative Example 20 parts by weight of a dicarbamate material prepared according to Example 1, part 1 of U.S. application Ser. No. 09/741,511 were mixed with 25 parts by weight of deionized water and 2.9 parts by weight of Nacure 5543 (available from King Industries, Norwalt, Conn.) using a laboratory air motor. The mixture was a low viscosity, heterogeneous product that phase separated into two layers on sitting overnight.

The invention has been described in detail with reference to preferred embodiments thereof. It should be understood, however, that variations and modifications can be made within the spirit and scope of the invention.

What is claimed is:

1. An aqueous composition, comprising
(a) water,
(b) a water-soluble, carbamate-functional material having a structure

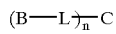

in which B represents β-hydroxy carbamate groups, each independently having a structure

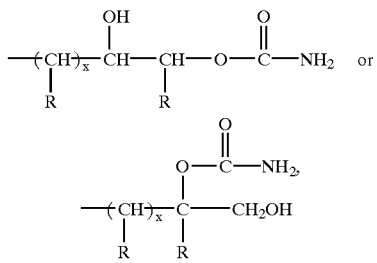

wherein each R is independently hydrogen, methyl, or ethyl and x is an integer of 1 to 3; L represents a linking group formed by a hydrogen acceptor group; C represents an n-functional central moiety; and n is a positive integer, and
(c) a second component dispersed or dissolved in the water by the water-soluble, carbamate-functional material.

2. A coating composition according to claim 1, comprising at least one crosslinker reactive with carbamate functionality.

3. A coating composition according to claim 2, wherein the crosslinker is a melamine formaldehyde resin.

4. A coating composition according to claim 1, wherein the composition includes from about 5% to about 70% of the compound (b).

5. A coating composition according to claim 1, wherein the composition includes from about 20% to about 60% of the compound (b).

6. A coating composition according to claim 1, wherein the composition is a clearcoat coating composition.

7. A coating on a substrate, comprising a layer of the cured composition of claim 1.

8. A composite coating on a substrate, comprising a layer of a basecoat coating and a layer of the cured clearcoat coating composition of claim 6.

9. A coating composition according to claim 1, further comprising a crosslinker reactive with active hydrogen functionality.

10. A coating composition according to claim 1, wherein the component (c) comprises a crosslinker reactive with active hydrogen functionality.

11. A coating composition according to claim 1, wherein the component (c) comprises a polymer.

12. A coating composition according to claim 11, wherein the polymer is selected from the group consisting of acrylic polymers, modified acrylic polymers, polyesters, polyepoxides, polycarbonates, polyurethanes, polyamides, polyimides, polysiloxanes, and combinations thereof.

13. A coating composition according to claim 11, wherein the polymer is an acrylic polymer having groups selected from hydroxyl groups, primary carbamate groups, and combinations thereof.

14. A coating composition according to claim 1, wherein the component (c) comprises an hydroxyalkyl carbamate compound or an hydroxyalkyl urea compound.

15. A coating composition according to claim 1, wherein the component (c) comprises a compound that is the reaction product of
(1) a compound comprising a primary carbamate group and an hydroxyl group and
(2) a compound that is reactive with hydroxyl groups on a plurality of molecules of compound (1), but that is not reactive with the carbamate groups on compound (1).

16. A coating composition according to claim 15, wherein compound (1) is a member selected from the group consisting of hydroxyethyl carbamate, hydroxypropyl carbamate, and hydroxybutyl carbamate.

17. A coating composition according to claim 15, wherein compound (2) is a member selected from the group consisting of the isocyanurate of isophorone diisocyanate and the isocyanurate of hexamethylene diisocyanate.

18. A coating composition according to claim 1, wherein the component (c) comprises a carbamate-functional or urea-functional material comprising at least two functional groups, at least one of which is a carbamate or urea group that is the reaction product of
(1) an hydroxyl group of a first compound that is the result of a ring-opening reaction between a compound with an epoxy group and a compound with an organic acid group and
(2) cyanic acid or a carbamate or urea group-containing compound.

19. A coating composition according to claim 1, wherein the component (c) comprises a carbamate-functional or urea-functional material that is the reaction product of
(1) a compound comprising a carbamate or urea group and an active hydrogen group that is reactive with (2), and
(2) a lactone or a hydroxy carboxylic acid.

20. A coating composition according to claim 1, wherein the component (c) comprises a carbamate-functional or urea-functional material that is the reaction product of
(A) the reaction product of
(1) a compound comprising a primary carbamate or primary urea group and an hydroxyl group and
(2) a lactone or a hydroxy carboxylic acid and
(B) a compound that is reactive with hydroxyl groups on a plurality of molecules of compound (A), but that is not reactive with the carbamate or urea groups on compound (A).

21. A coating composition according to claim 1, wherein the component (c) comprises a carbamate-functional or urea-functional material that is the reaction product of
(A) the reaction product of
(1) a compound comprising a primary carbamate or primary urea group and an hydroxyl group and
(2) a lactone or a hydroxy carboxylic acid and
(B) a compound that converts an hydroxyl group on (A) to a carbamate group, or a compound comprising a group that is reactive with a hydroxyl group and a carbamate or urea group or group that can be converted to carbamate or urea.

22. A coating composition according to claim 1, wherein the component (c) comprises a carbamate-functional material that is the reaction product of
(1) a first material that is the reaction product of a mixture including at least a polyisocyanate and an active hydrogen-containing chain extension agent with
(2) a compound comprising a group that is reactive with said first material and a carbamate group or group that can be converted to a carbamate group.

23. A coating composition according to claim 1, wherein the component (c) comprises a material having at least two carbamate groups and a hydrocarbon moiety having about 24 to about 72 carbon atoms.

24. A coating composition according to claim 23, wherein the material has from two to four carbamate groups.

25. A clearcoat coating composition according to claim 23, wherein the material has two carbamate groups.

26. A coating composition according to claim 23, wherein the hydrocarbon moiety has from about 36 to about 72 carbon atoms.

27. A coating composition according to claim 23, wherein the hydrocarbon moiety has from about 36 to about 54 carbon atoms.

28. A coating composition according to claim 23, wherein the hydrocarbon moiety has about 36 carbon atoms.

29. A coating composition according to claim 1, wherein the component (c) comprises a material having a structure selected from the group consisting of

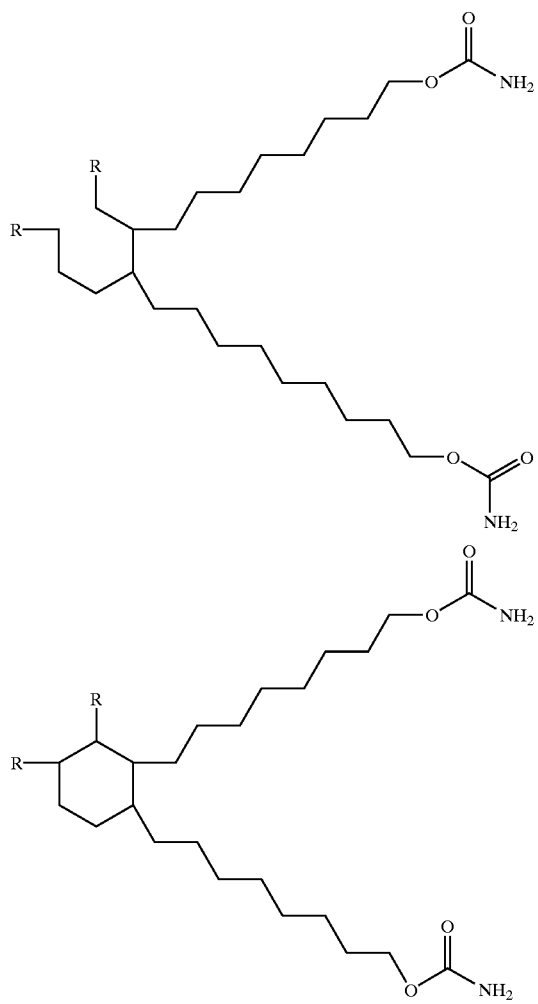

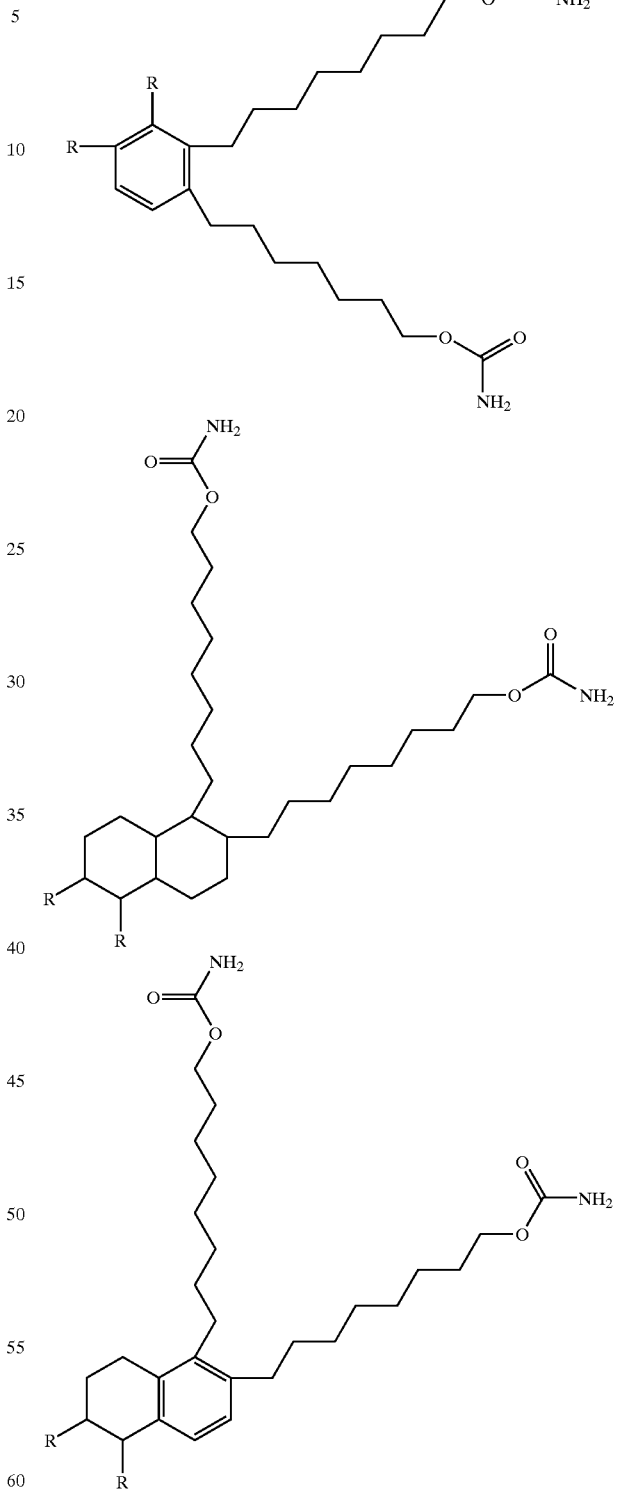

wherein each R group is independently an alkyl of 5 to 8 carbon atoms.

* * * * *